(12) United States Patent
Fedder et al.

(10) Patent No.: US 12,096,553 B2
(45) Date of Patent: Sep. 17, 2024

(54) INTEGRATED ELECTRONIC DEVICE WITH FLEXIBLE AND STRETCHABLE SUBSTRATE

(71) Applicant: CARNEGIE MELLON UNIVERSITY, Pittsburgh, PA (US)

(72) Inventors: Gary K. Fedder, Turtle Creek, PA (US); Carmel Majidi, Pittsburgh, PA (US); Philip R. LeDuc, Wexford, PA (US); Lee E. Weiss, Pittsburgh, PA (US); Christopher J. Bettinger, Pittsburgh, PA (US); Naser Naserifar, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 1181 days.

(21) Appl. No.: 16/572,652

(22) Filed: Sep. 17, 2019

(65) Prior Publication Data
US 2020/0029428 A1   Jan. 23, 2020

Related U.S. Application Data

(60) Division of application No. 15/923,442, filed on Mar. 16, 2018, now Pat. No. 10,462,897, which is a
(Continued)

(51) Int. Cl.
*H05K 1/02*     (2006.01)
*B29C 33/40*   (2006.01)
*H01L 21/48*   (2006.01)
*H05K 1/18*     (2006.01)
*H05K 3/30*     (2006.01)
(Continued)

(52) U.S. Cl.
CPC ........... *H05K 1/0283* (2013.01); *B29C 33/40* (2013.01); *H01L 21/4803* (2013.01); *H05K 1/02* (2013.01); *H05K 1/185* (2013.01); *H05K 3/30* (2013.01); *H05K 3/38* (2013.01); *H05K 3/4644* (2013.01); *A61B 2562/125* (2013.01); *A61B 2562/164* (2013.01); *B05D 3/10* (2013.01); *B05D 3/107* (2013.01); *B05D 3/108* (2013.01); *H01L 23/3121* (2013.01); *H05K 5/065* (2013.01); *H05K 2201/1003* (2013.01)

(58) Field of Classification Search
CPC .......................... B05D 3/10; B05D 3/107–108
USPC ................ 361/749, 760–762, 767, 782–784, 361/777–778, 803; 174/250–261, 520
See application file for complete search history.

(56) References Cited

U.S. PATENT DOCUMENTS 8,861,220 B2 * 10/2014 Loher .................... H05K 1/038
                                                                   361/776
9,171,794 B2 * 10/2015 Rafferty .................. H01L 24/82
(Continued)

*Primary Examiner* — Tuan T Dinh
(74) *Attorney, Agent, or Firm* — Michael G. Monyok

(57) ABSTRACT

A flexible and stretchable integrated electronic device includes a substrate having a stiffness gradient, wherein a rigid electronic device is embedded within the substrate. The stiffness gradient within the substrate prevents delamination at the interface between the substrate and the embedded device. The stiffness gradient is accomplished by providing at least two distinct zones in the substrate with uniform stiffness, with each zone decreasing in stiffness as in a distance from the embedded device increases, or the gradient is accomplished by having a zone with a varying stiffness.

4 Claims, 14 Drawing Sheets

Related U.S. Application Data continuation-in-part of application No. PCT/US2017/021974, filed on Mar. 10, 2017.

(60) Provisional application No. 62/389,853, filed on Mar. 10, 2016.

(51) Int. Cl.
| | |
|---|---|
| *H05K 3/38* | (2006.01) |
| *H05K 3/46* | (2006.01) |
| B05D 3/10 | (2006.01) |
| H01L 23/31 | (2006.01) |
| H05K 5/06 | (2006.01) |

(56) References Cited

U.S. PATENT DOCUMENTS

| | | | |
|---|---|---|---|
| 9,899,330 B2 * | 2/2018 | Dalal | H01L 21/56 |
| 10,477,688 B2 * | 11/2019 | Aleksov | H05K 1/189 |
| 2011/0240747 A1 * | 10/2011 | Stewart | G06K 19/07758 |
| | | | 235/492 |
| 2012/0091594 A1 * | 4/2012 | Landesberger | H01L 24/83 |
| | | | 257/E23.068 |
| 2013/0131482 A1 * | 5/2013 | Fedder | A61B 5/291 |
| | | | 264/494 |
| 2013/0176689 A1 * | 7/2013 | Nishimura | H01L 23/3121 |
| | | | 29/832 |
| 2013/0333094 A1 * | 12/2013 | Rogers | A61B 34/76 |
| | | | 340/407.1 |
| 2014/0240932 A1 * | 8/2014 | Hsu | H05K 1/028 |
| | | | 361/749 |
| 2017/0181275 A1 * | 6/2017 | Dias | H05K 1/111 |
| 2018/0066299 A1 * | 3/2018 | Kim | C12M 23/02 |

* cited by examiner

INTEGRATED ELECTRONIC DEVICE WITH FLEXIBLE AND STRETCHABLE SUBSTRATE

CROSS-REFERENCE TO RELATED APPLICATIONS

This application is a divisional of U.S. Nonprovisional application Ser. No. 15/923,442 filed Mar. 16, 2018, which is a continuation of Application No. PCT/US17/21974 filed on Mar. 10, 2017, which claims the benefit under 35 U.S.C. § 119 of Provisional Application Ser. No. 62/389,853, filed Mar. 10, 2016, each of which is incorporated herein by reference.

STATEMENT REGARDING FEDERALLY SPONSORED RESEARCH

This invention was made with Government support under 1547810-CBET and 1100430-CMMI awarded by the National Science Foundation. The Government has certain rights in this invention.

BACKGROUND OF THE INVENTION

The invention relates generally to flexible and stretchable electronics. More specifically, the invention relates to an integrated device comprising a substrate with an embedded rigid electronic device, where the substrate has a stiffness gradient around the embedded device to allow flexible and stretchable movement of the integrated device.

Flexible and stretchable electronics have emerged as a new technology for realizing smart sensors and actuators for applications ranging from medicine to personal electronic devices. Such systems have been evolving at a rapid rate with the promise of integration into areas such as the human body. However, integrating rigid electronics with a flexible substrate (i.e. the human body) poses problems resulting from the mismatch in compliance between the two materials.

Stretchable electronics have been pursued through a wide variety of techniques including organic electronic materials such as conductive polymers, nanowires, microfluidic circuits, and thin inorganic materials patterned on soft polymers. An elusive goal of these approaches is to simultaneously achieve the performance and reliability of established foundry electronic devices in a stretchable platform. However, the goal is unmet as these designs suffer from relatively poor transistor density and performance in addition to uncertain reliability.

Inorganic materials such as silicon processors have been used in electronic devices for decades and embedding these materials in stretchable and flexible structures would provide integrated functionality and reliability. However, delamination of the rigid processor from the soft substrate has inhibited the impact of this approach. To overcome this problem, one method attempts to use sub-micron layers of inorganic materials within an electronic device, which allows the stiff materials to have a higher degree of flexibility. However, thinning the devices causes significant challenges for integrating silicon-based electronics as the interconnect stack for complementary metal-oxide semiconductors (CMOS), for example, is well over 1 µm in thickness and is over 10 µm thick for state-of-the-art CMOS available from foundries. These devices cannot be easily thinned.

Along with the challenges in the lack of flexibility of these silicon-based electronics is the mechanical response associated with embedding them into flexible materials. For example, there is a significant mismatch in mechanical properties of silicon-based electronics (Young's modulus, E≈170 GPa) and soft materials mimicking those of the human body (Young's modulus, E≈100 kPa). This mismatch causes difficulties in the attachment, stretching, and functionality for wearable biomedical instruments. Silicon-based electronics that are rigid and planar have a fracture strain less than 2%, while flexible and stretchable electronics can be bent, stretched, and twisted with typical failure strain greater than 10%.

As another approach to overcome the mismatch problem, thin polymer films that are relatively stiff compared with stretchable materials are embedded into stretchable substrates in order to suppress the onset of interconnect and device breakage. In one example of this approach, patches of polyethylene terephthalate are embedded within a softer polymer to help suppress strain local to the device substrate and increase the shear area, demonstrating operation up to 100% uniaxial stretching and 300% localized internal strain. However, the general intent of locally suppressing strain works when the electronic devices are on the surface of the substrate since no interface exists for normal stress to cause delamination in this configuration.

It would therefore be advantageous to develop a flexible and stretchable substrate incorporating traditional electronic devices that prevents delamination between the materials.

BRIEF SUMMARY

According to embodiments of the present invention is an integrated electronic device comprising a rigid electronic device embedded within a substrate having variable stiffness. More specifically, the substrate demonstrates a stiffness gradient with the greatest stiffness adjacent to the rigid electronic device. By creating a gradient, the incidence of delamination of the substrate from the embedded device is decreased when the integrated device is stretched or flexed.

The integrated device allows the use of "thick" silicon chips (e.g., thickness greater than 10 µm) mimicking CMOS electronic chips for wearable system applications such as biomedical health monitors that interface with the skin where large deformation can occur. Further, in this configuration the peak strain experienced in the device is moved away from the rigid device/elastomeric interface. Eliminating the delamination effects between the soft and rigid material is required for design of stretchable systems that will embed standard microfabricated electronics (i.e., CMOS), especially in wearable applications. In addition, the integrated device allows the use of wires without breaking under strain.

DETAILED DESCRIPTION

Figure 1A:
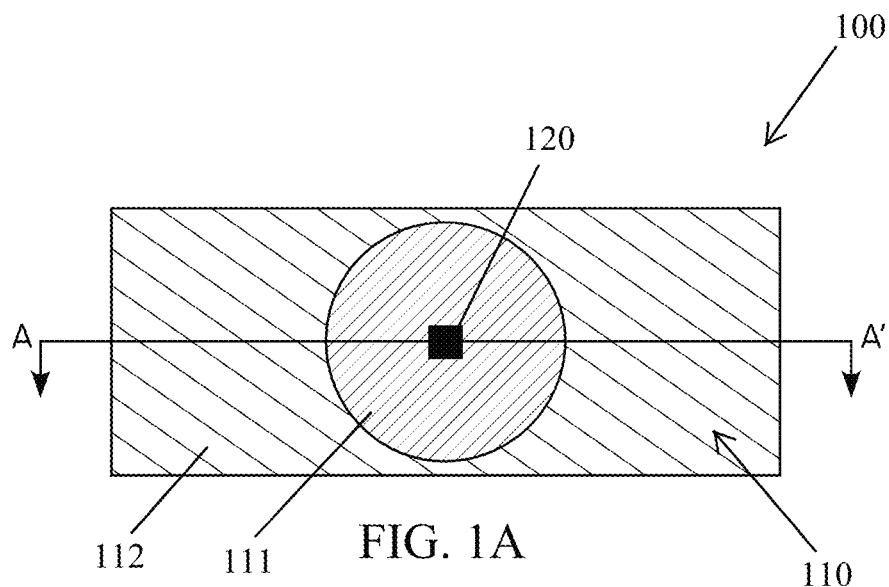
FIGS. 1A-1C show the integrated device, according to one embodiment.
Figure 1B:
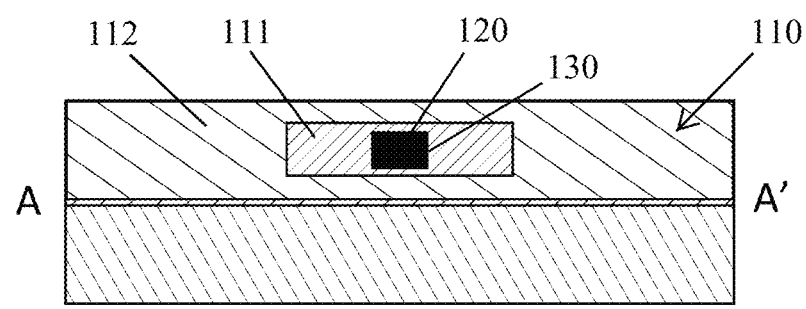
Figure 1C:
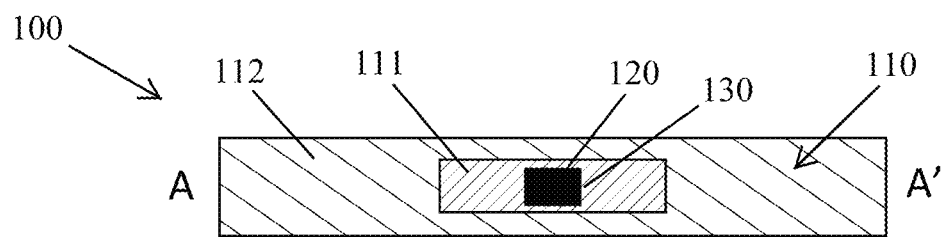

According to one embodiment of the present invention is an integrated electronic device 100 comprising a flexible and stretchable substrate 110 and a rigid electronic device 120. As shown in the embodiment depicted in FIG. 1A, the substrate 110 comprises a plurality of sections, where each section has a different stiffness. More specifically, the substrate 110 of the embodiment shown in FIG. 1A comprises a first section 111 and a second section 112, where the first section 111 has a greater stiffness than the second section 112. As further shown in FIGS. 1A-1B, the rigid electronic device 120 is embedded within the first section 111 of the substrate 110.

By providing a gradient in the stiffness of the substrate 110, delamination at the interface 130 between the rigid electronic device 120 and the substrate 110 can be reduced by controlling the strain and stress contours at the interface 130 of the rigid electronic device 120 and substrate 110 when the substrate 110 is stretched. That is, the presence of the intermediate soft material (first section 111) with a Young's modulus between that of the primary soft material (second section 112) and the embedded device 120 decreases the risk of delamination as the majority of the strain will be accommodated in the second section 112 or outer regions of the substrate 110. Because of this, the substrate material near interface 130 with the rigid electronic device 120 experiences relatively low strain and stress.

While example embodiments will be discussed in terms of a first section 111 and a section 112, the substrate 110 may comprise additional sections to further smooth the stiffness gradient. In alternative embodiments, a continuous stiffness gradient is employed on the substrate 110 without distinct sections. In yet another embodiment, a first section 111 has a uniform stiffness while the second section 112 has a stiffness gradient. The presence of distinct sections or a continuous gradient in the substrate depends, in part, on the particular fabrication method employed.

As previously stated, the stiffness gradient aims to prevent delamination at the interface 130 of the embedded device 120 and the flexible substrate 110. To quantify the delamination characteristic of the interface 130, the 'energy release rate', G in units of $J/m^2$, is used to guide the fabrication of the integrated flexible electronic device 100. In testing, the energy introduced to a pre-formed crack, which causes it to increase in size, must be balanced by the amount of energy lost due to the formation of new surfaces and other dissipative processes, such as plasticity. The crack size increases when the energy release rate equals a critical value, the fracture energy denoted as $\Gamma$.

Figure 2:
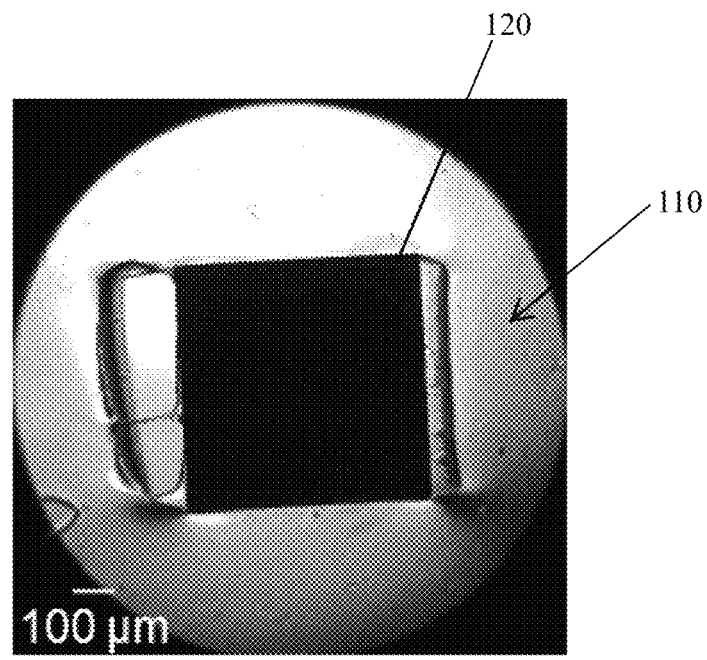
FIG. 2 is an image showing delamination at the interface of the rigid device and the substrate.
Figure 3:
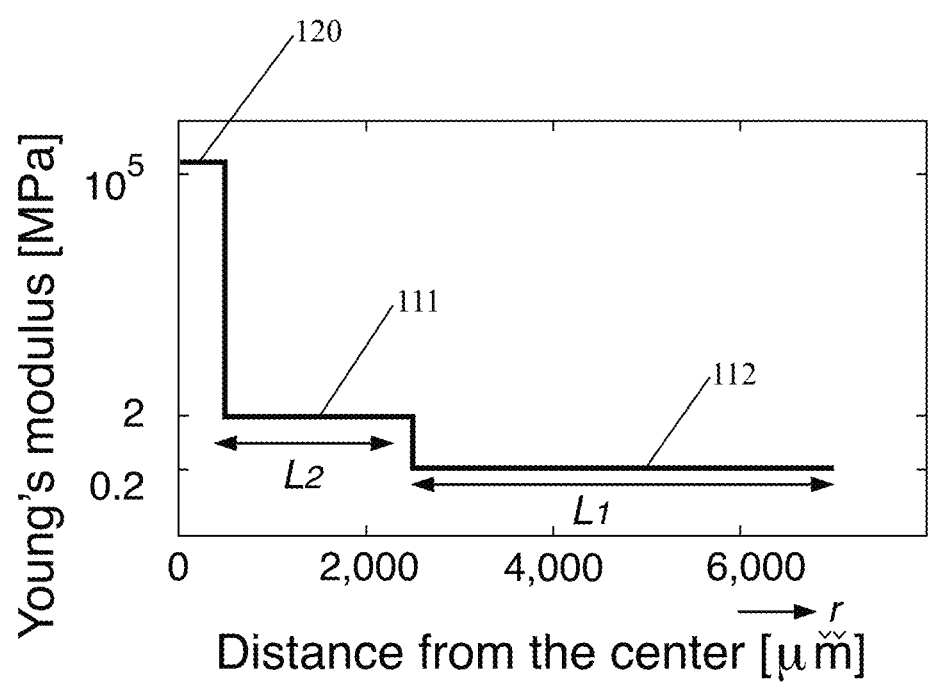
FIG. 3 is a graph depicting the stiffness of various components of the integrated device.

The risk of delamination at the interface 130 between a soft material and rigid material is significant and this risk increases when the system is stretched and thus subjected to mechanical strain. Therefore, if the structure has sufficiently high stress at the interface 130 between the two materials, delamination occurs (see FIG. 2). To address this challenge, the amount of strain and strain energy in the soft material (i.e. substrate 110) at the interface 130 should be minimized to prevent delamination. This minimization is accomplished using the intermediate material gradient such that the mechanical stiffness properties between the soft and rigid materials are changed gradually (see FIG. 3). Adding a single intermediate material in the first section 111 of the substrate 110, where the first section 111 has a stiffness value between the soft second section 112 and the rigid embedded device 120, has a significant effect in reducing delamination and allows for the integration of rigid devices 120, such as CMOS chips.

In one embodiment, the substrate 110 that surrounds the silicon-based electronic device 120 is made of two soft polymers with different Young's modulus, $E_1$ and $E_2$ ($E_2 > E_1$). The stiffer intermediate polymer (Young's Modulus $E_2$) is in contact with the silicon-based device 120 while the softer material (Young's Modulus $E_1$) occupies the outer domain. When the composite substrate 110 is strained, the outer, second portion 112 has a higher strain when compared to the intermediate inner first portion 111. The value of Young's modulus ($E_2$) of the intermediate material has an effect in minimizing the delamination in the flexible integrated device 100.

Figure 4:
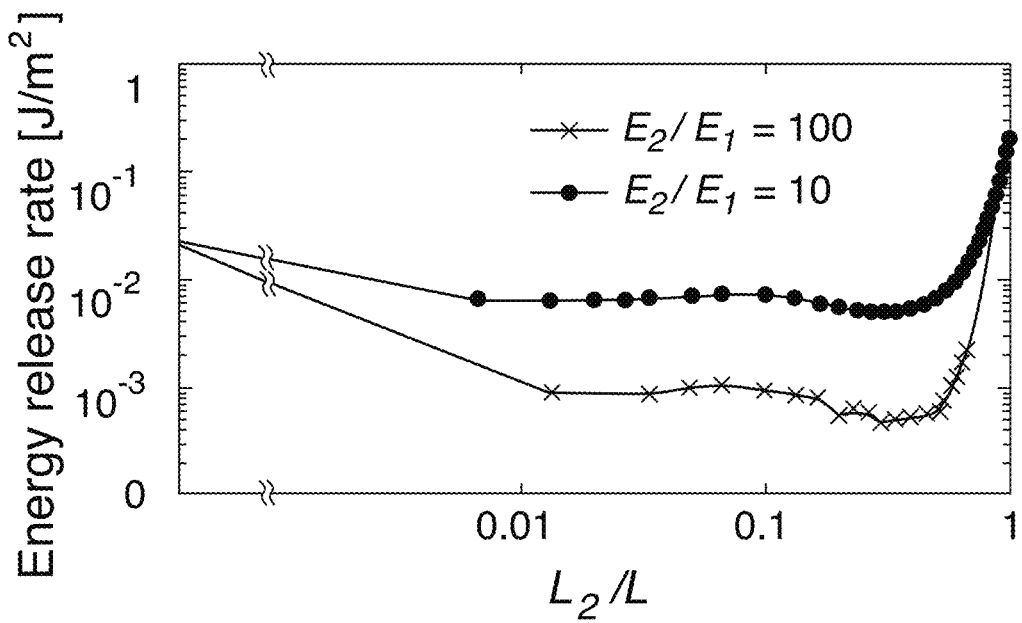
FIGS. 4-5 are graphs showing the energy release rate for integrated devices with varying parameters.
Figure 5:
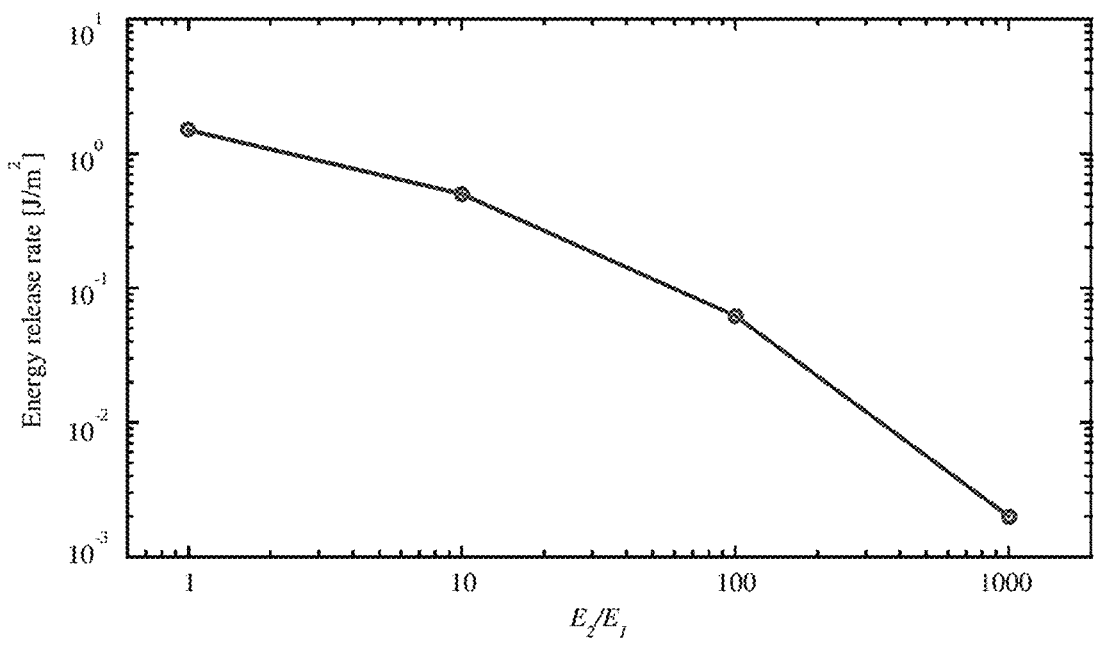

For example, the effect of the ratio, $E_2/E_1$, can be determined by calculating the energy release rates using techniques such as a two-dimensional finite element analysis (FEA). The two conditions $E_2/E_1=10$ and $E_2/E_1=100$ shown in FIG. 4 indicate the significance of the Young's modulus ratio on delamination of layers. The energy release rate values for additional ratios are shown in FIG. 5. As shown in FIG. 4, the system having the higher Young's modulus ratio has the lowest energy release rate for all values of $L_2$, which corresponds to the length or radius of the first section 111. As the energy release rate rises with external applied strain, the system with the higher Young's modulus ratio results in a larger safe region where delamination does not occur. Of note, for any case where a first portion 111 and second portion 112 are used, the energy release rate is lower when compared to just a single soft material having either Young's modulus $E_1$ or $E_2$.

Figure 6A:
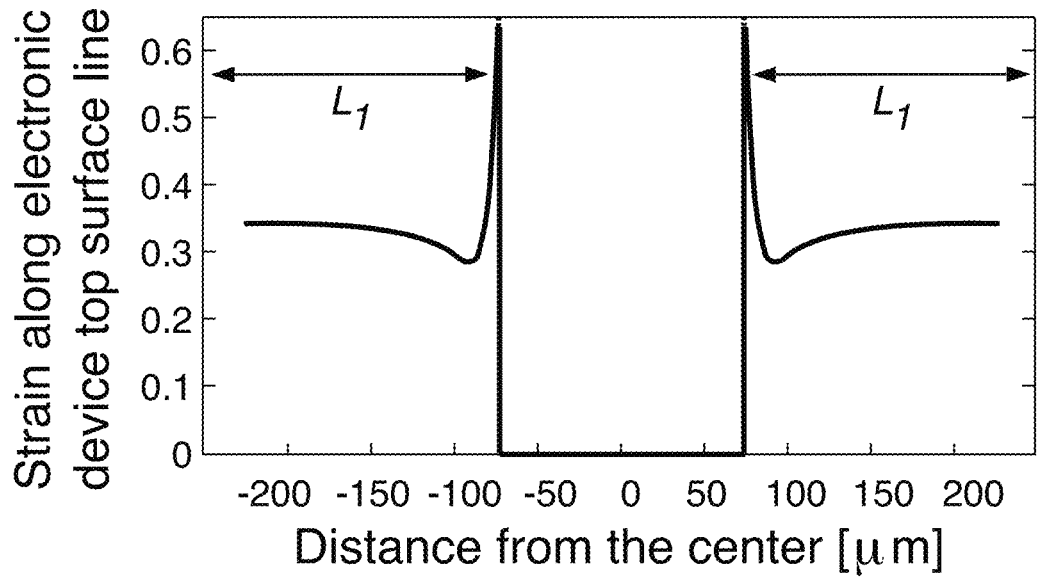
FIGS. 6A-6B show the strain in the device as a function of the distance from a center.
Figure 6B:
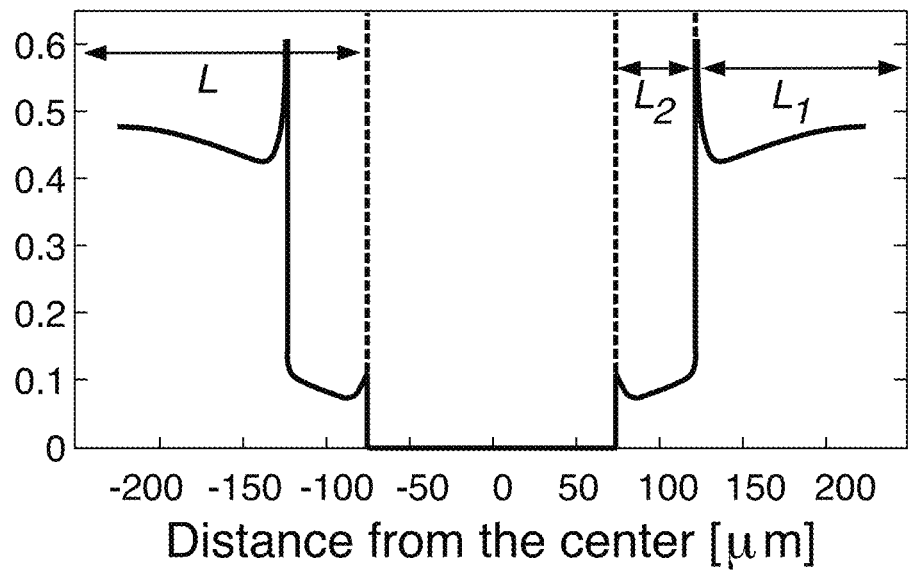

Results from an example finite-element analysis are shown in FIGS. 6A-6B. Maximum principal elastic strain for two structures without (FIG. 2A) and with (FIG. 2B) the engineered two-section substrate 110, indicate the amount of strain in the cut-plane coinciding with the top surface of silicon device 120. The strain at the interface 130 between the silicon electronic device 120 and the intermediate first portion 111 in the engineered substrate 110 is approximately six times smaller than in the example substrate 110 having only a single material. This lower strain region at the chip interface 130 to the engineered substrate 110 reduces the onset of delamination from the embedded electronic device 120.

In the example shown in FIG. 6B, the highest strain occurs at the interface between the first section 111 and the second section 112. Accordingly, this region is the most susceptible to delamination. However, by selecting two materials with strong bonding capability, the substrate 110 can be designed to withstand higher strains before delamination. In one embodiment, the substrate comprises polydimethylsiloxane (PDMS) with a differing amount of elastomer base-to-curing agent mixing ratio in each section. PDMS with different base-to-curing agent mixing ratios exhibit strong bonding. In addition, the bonding between the two sections 111, 112 can be enhanced by selecting materials with high surface adhesion. Also, in general, an enhanced roughness at the border between the two has a positive effect on bonding between the two soft materials. In alternative embodiments, other elastic polymers are used in the substrate 110. For example, the substrate 110 may comprise two-part silicone elastomers, including but not limited to: RTV (room-temperature-vulcanizing) silicone rubber, tin-catalyzed silicones, and platinum-catalyzed silicones (e.g., Ecoflex™ from Smooth-On, Inc., Macungie, Pa.).

In order to compare variations in the two-section substrate 110, three example embodiments (listed in Table 1) are analyzed. In these examples, the rigid electronic device 120 is a 1 mm×1 mm×50 μm silicon chip. For the compliant substrate 110, two mixtures of PDMS with a base-to-curing agent ratios of 5:1 and 20:1 are used. The Young's modulus of PDMS relates to the ratio of monomer (base) and hardener (curing agent). Using PDMS with different ratios of base and curing agent for the materials of the first section 111 and second section 112 allows the Young's modulus values to be modified between regions while still achieving strong bonding at their interface. The substrate 110 in examples #1 and #2 are made completely of a single type of PDMS, while the substrate 110 in example #3 implements the composite structure with a first section 111 and a second section 112 of PDMS each having different stiffness.

TABLE 1

| Sample | 1st Material | 2nd Material | Energy Release |
|---|---|---|---|
| #1 | PDMS (5:1), L = 3 mm | none | 10.99 J/m² |
| #2 | PDMS (20:1), L = 3 mm | none | 1.493 J/m² |
| #3 | PDMS (20:1), L = 2 mm | PDMS (5:1), L = 1 mm | 0.689 J/m² |

The energy release rate, which indicates the likelihood of delamination, was determined for a given interface using a FEA with a symmetric quarter model of the entire substrate. A fine mesh was placed on an initial 10 μm-wide separation (i.e., a crack initiator) located at the interface 130 between the sidewall of the rigid device 120 and the surrounding PDMS substrate 110. The crack with the highest degree of stress was located at the corner of the device 120. The energy release rate was determined by subtracting the strain energy before and after crack growth, while dividing by the area of the crack. Mesh refinements were used to verify numerical convergence.

Table 1 indicates that the energy release rate in the stiffest substrate (PDMS (5:1)) used in sample #1 is over 7 times higher than the energy release rate in the intermediate stiffness substrate 110 (PDMS (20:1)) used in sample #2. The energy release rate for sample #3 was found to be approximately two times lower than the next best case of sample #2. When the energy release rate exceeded a critical value, as determined empirically, the crack propagated and the substrate 110 delaminated from the embedded rigid device 120. As a result of the lowest energy release rate occurring for sample #3, the risk of delamination at the interface 130 was low and the bonding at the interface 130 remained intact.

To compare FEA predictions shown in Table 1 and to quantify the onset of strain failure, tensile tests were performed for all three sample types. In many applications, the rigid device 120 will often be no greater than 1 mm in size and sparsely embedded within the substrate 110, while the radius of bending curvature of the soft substrate 110 is expected to be much greater than 1 mm. Tensile strain loading at each end of the substrate was applied as a series of small incremental step functions. The system was elongated at a low strain rate (0.001 s⁻¹) to achieve a pseudo steady-state and the strain failure was examined through optical microscopy imaging. Delamination for sample #1 occurred at 20% strain, as indicated by a crack initiation and subsequent growth. The strain for delamination for sample #2 was higher, occurring at 30% strain at the interface 130 and in line with the finite-element predictions (see Table 1). The silicon-PDMS (5:1) interface 130 in sample #3 did not delaminate. Instead, crack growth occurred at the interface of the PDMS (5:1) and PDMS (20:1) materials between the first section 111 and second section 112, rather than at the interface 130 with the embedded device 120, and initiated at 100% strain. This strain failure threshold was six times larger than that of sample #1 (with the silicon-PDMS (5:1) interface). Further, the strain cycling performance of sample #3 up to 100 cycles under maximum 50% strain was studied and delamination was not detected at either interface.

While the foregoing analyzes the effect of material stiffness on the risk of delamination, the relative length of each section 111, 112 of the substrate 110 also have an effect. To minimize the delamination risk, the substrate 110 can be analyzed based on the ratio of the length of first section, $L_2$, to the total substrate length, $L=L_1+L_2$. The energy release rates for different values of the $L_2/L$ ratio at the interface 130 of silicon-PDMS (5:1) and at the interface 130 of PDMS (5:1)-PDMS (20:1) were calculated.

At these interfaces, material properties and geometric design parameters affect the energy release rate function:

$$G=f(\alpha, E_1, E_2, \varepsilon, L_1, L_2, h_1, h_2, h_3) \quad (1)$$

where α is crack length, ε is the applied strain, $h_1$ is the thickness of the material in the second section 112 of substrate 110 on top of the embedded device 120, $h_2$ is the thickness of the material in the first section 111 on top of the embedded device 120, and $h_3$ is the thickness of the embedded device 120.

Figure 7A:
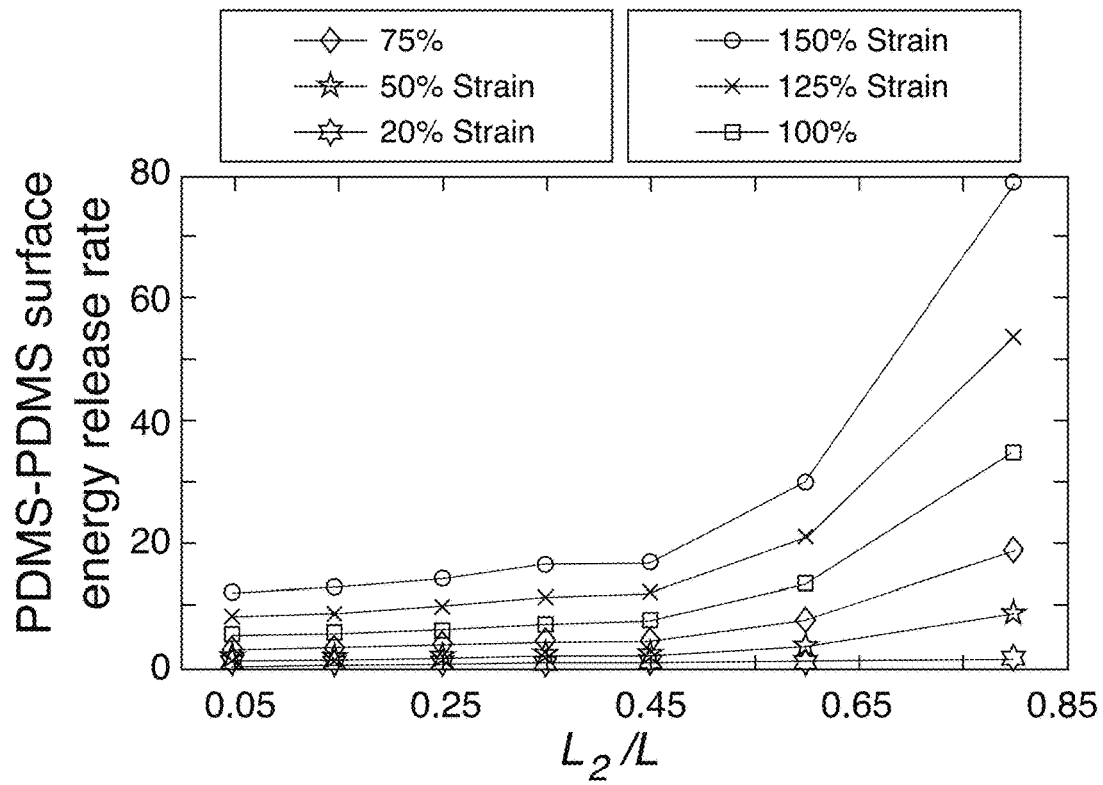
FIGS. 7A-7B are graphs depicting energy release rates.
Figure 7B:
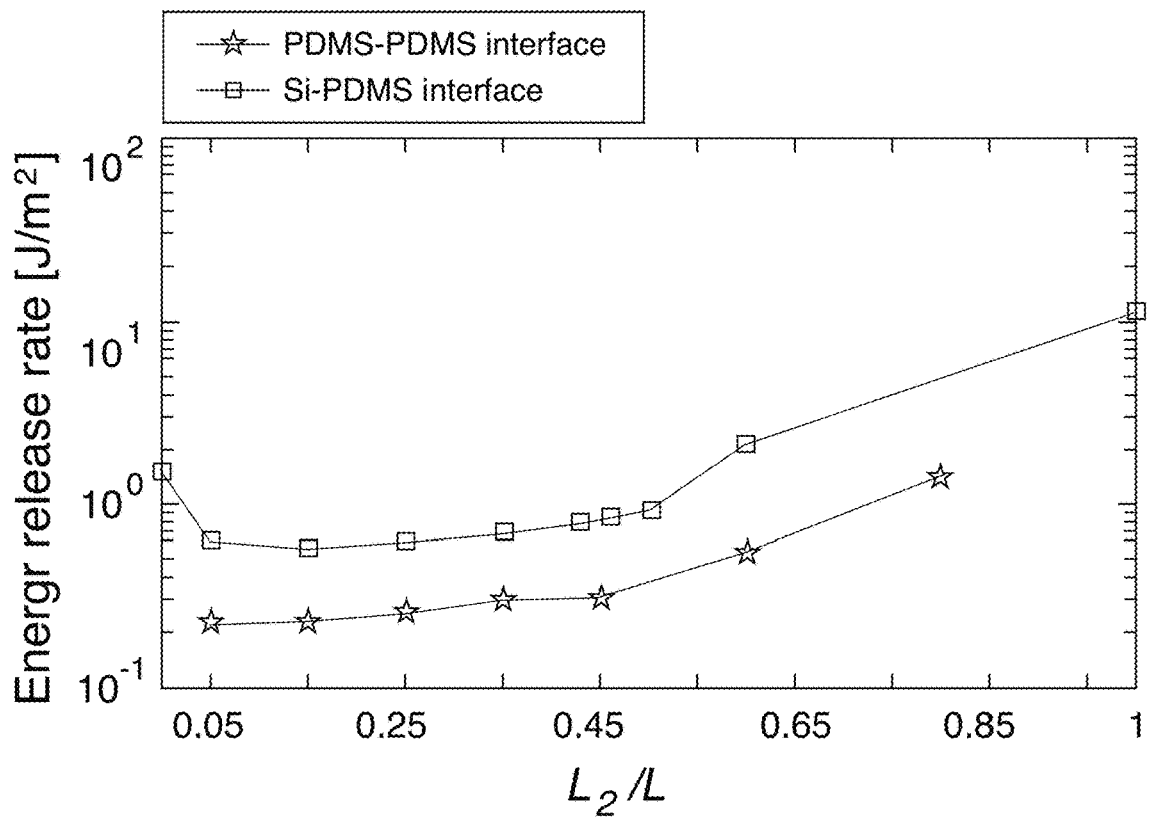

For this comparison, all parameters except $L_2$ are fixed. The energy release rate increases with increasing applied strain with approximately quadratic dependence. This nonlinear dependence of G on strain arises in FIG. 7A, which also illustrates a nonlinear dependence on $L_2$. A comparison in FIG. 7B of energy release rates at 20% strain for the interface 130 (top line) and for the first section 111/second section 112 (PDMS (5:1)/PDMS (20:1)) interface (bottom line) indicates that G for the silicon-PDMS interface 130 is roughly two times higher than for the PDMS-PDMS interface. In FIG. 7B, $L_2/L=0$ represents the sample #1 case and $L_2/L=1$ represents the sample #2 case, with these endpoint values corresponding to those in Table 1. For intermediate values of $L_2/L$, the energy release rate at the silicon-PDMS interface 130 decreases significantly.

Figure 8:
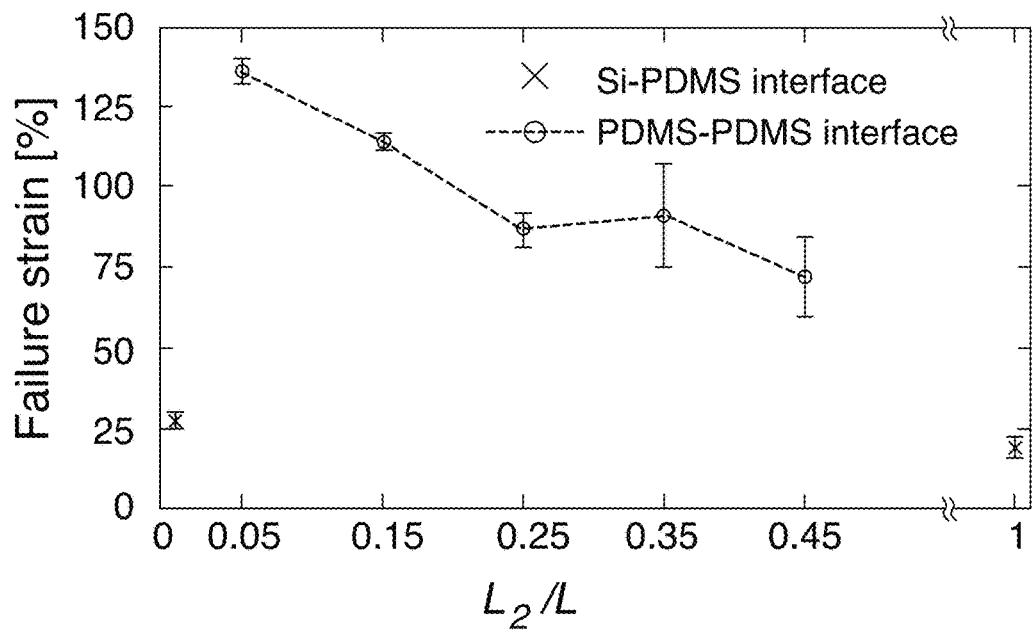
FIG. 8 shows the failure strain at various interfaces.
Figure 9:
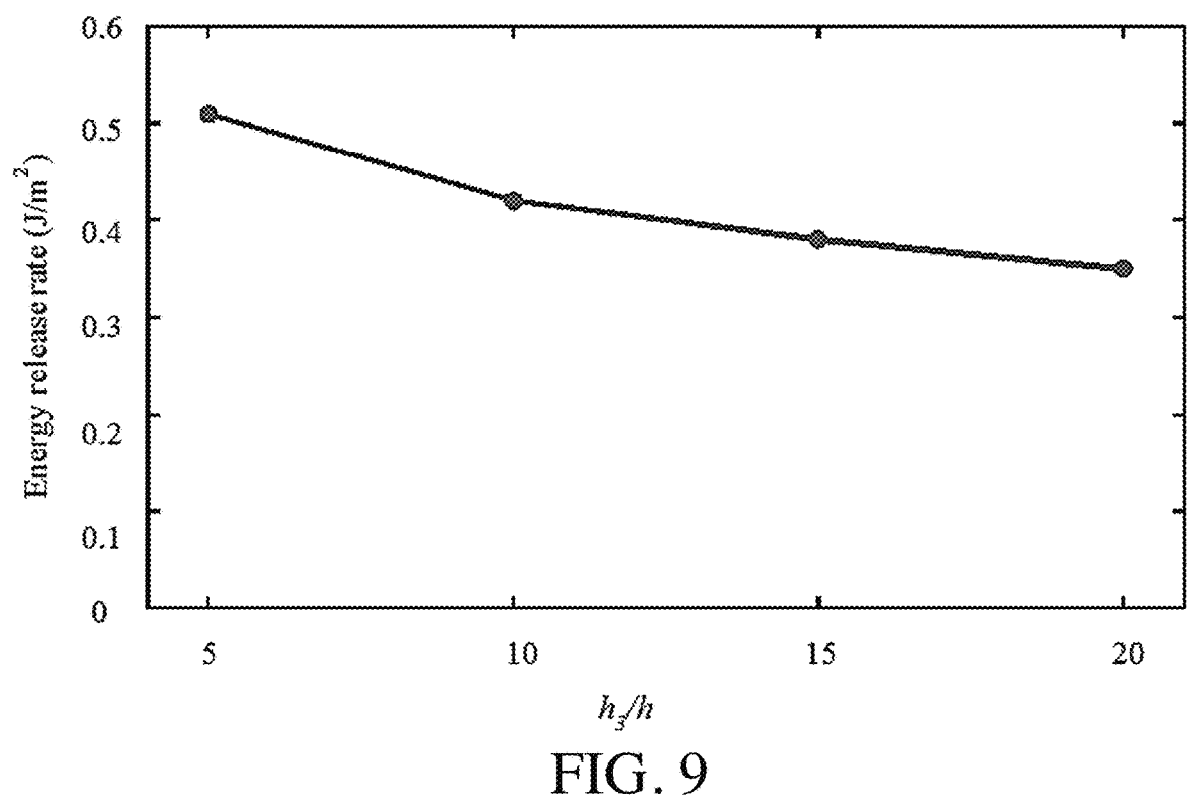
FIGS. 9-11 are graphs depicting energy release rates.
Figure 10:
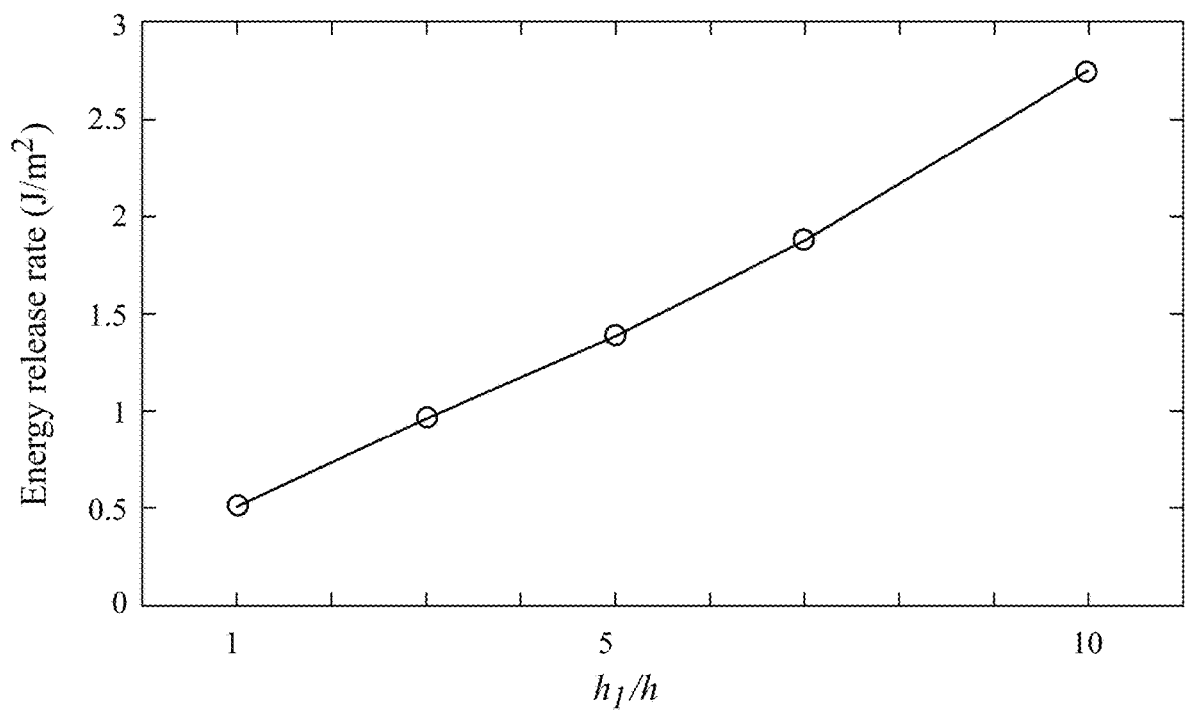
Figure 11:
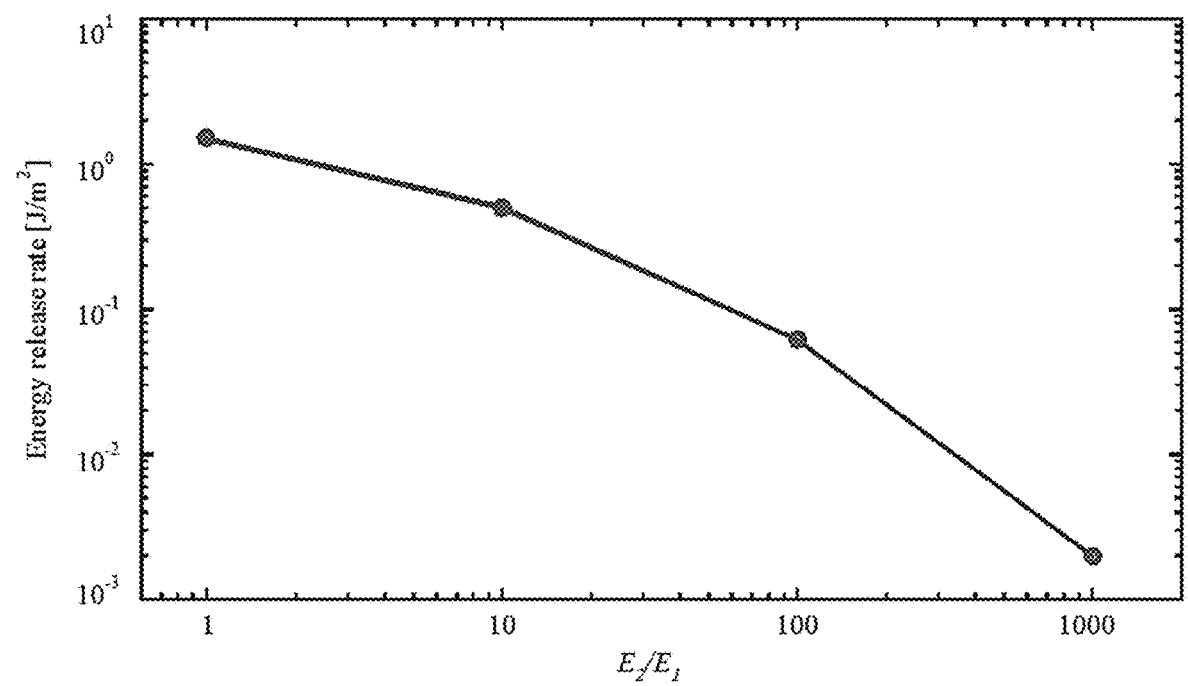

FIG. 8 shows the tensile responses of integrated devices 100 with different $L_2/L$ (0.05, 0.15, 0.25, 0.35, 0.45) and a fixed L=10 mm. The graph of FIG. 8 shows the quantified the strain level at the onset of delamination and indicates in all cases that the interface between the first section 111 and second section 112 failed first. The failure strain values for the example without an intermediate stiffness first section 111 ($L_2/L=0$ and $L_2/L=1$) were relatively small. The highest failure strain of 140% occurred with the geometric condition of $L_2/L=0.05$ (see FIG. 8). The effects on G of $h_3/h_2$, $h_1/h_2$, and $E_2/E_1$ are shown in FIGS. 9, 10, and 11, respectively. Delamination typically happens at corners, edges and regions of the device/substrate interface 130 where there is high strain. Having rounded corners or circular chips can reduce the energy release rate.

It is estimated that the adhesion energy of Si-PDMS interfaces is about 0.05-0.4 J/m$^2$. The work of adhesion for a PDMS-PDMS interface is in the range of about 250-300 J/m$^2$. Therefore, the PDMS-PDMS bonding is stronger than Si-PDMS bonding by four orders of magnitude. While the Si-PDMS adhesion could possibly be enhanced through a geometric interlock design or through use of adhesion promoters, the substrate 110 of the present invention moves the critical interface to the interface of the first section 111 and the second section 112, enabling exploitation of the natural adhesion between similar polymers.

To create a substrate 110 having a gradient, PDMS with mixing ratios of base to curing agent of (5:1) and (20:1) were used in the example embodiment described above. However, in alternative embodiments, other mixing ratios, additional materials, or distinct materials can be used to create the gradient. In the example embodiment, the Young's modulus values are $E_2$=1.98 MPa for PDMS (5:1) and $E_1$=0.26 MPa for PDMS (20:1).

One fabrication method comprises embedding a 1 mm×1 mm×50 μm silicon chip (E=170 GPa) as the rigid device 120 into a 90 μm-thick PDMS sheet as the substrate 110. To make the two-material substrate 110, a handle wafer as a base 141 is spin coated with 10 μm-thick PDMS (5:1), which will become part of the first portion 111 of the substrate 110. The coating step can be followed by partial curing at 80° C. for 20 minutes to allow the film to solidify without losing its adherent nature. Next, the silicon chip (i.e. device 120) is then transferred to this first layer, and a second 60 μm-thick PDMS (5:1) layer is spin coated and then cured at 80° C. for 4 hrs., thereby embedding the rigid device 120 in the first portion 111 of the substrate 110. This composite structure is then etched (for example, reactive ion etching using SF$_6$ and O$_2$ plasma) into a 1 mm diameter circle and released from the base 141 and subsequently transferred to a second base 141 having an initial 10 μm-thick spin-coat PDMS (20:1) layer, which will be part of the second portion 112. The composite structure is then embedded into PDMS (20:1) by spin coating an additional 80 μm-thick PDMS (20:1) layer followed by 4 hrs. curing at 80° C. The soft PDMS (20:1) material of the second portion 112 covers the first portion 111 by approximately 10 μm on its top and bottom surfaces. Thus, in this embodiment of the method of fabrication, there are two general stages: first, embedding the rigid device 120 into the first portion 111 of the substrate 110; and, second, embedding the combined structure into the second portion 112 of the substrate 110.

In an alternative embodiment, the base 141 is coated with a submicron layer of gelatin (1%). Gelatin is used as a sacrificial layer 143 (see FIG. 1B) since it is soluble in water and it aids in release of the device 100. For example, the device 100 can be released in hot water (70° C.) since gelatin is highly soluble at this temperature level. In yet another embodiment, the combined embedded device 120/first portion 111 composite structure is patterned into a circular shape using a hard mask through reactive-ion etching using SF$_6$/O$_2$ plasma for 3 hrs.

Figure 12A:
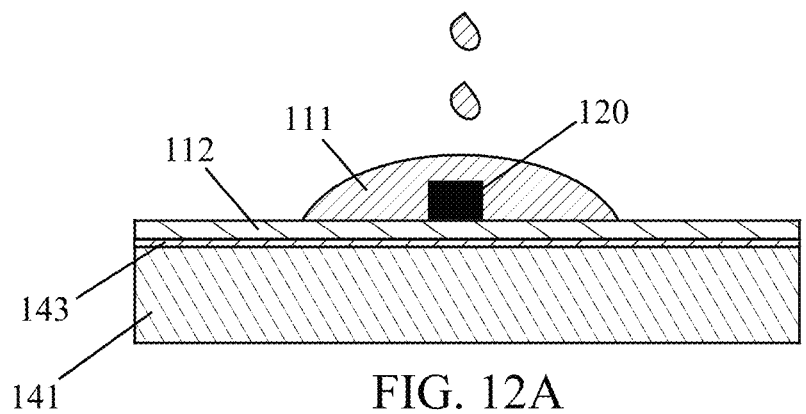
FIGS. 12A-12C depict a fabrication method of the integrated device according to one embodiment.
Figure 12B:
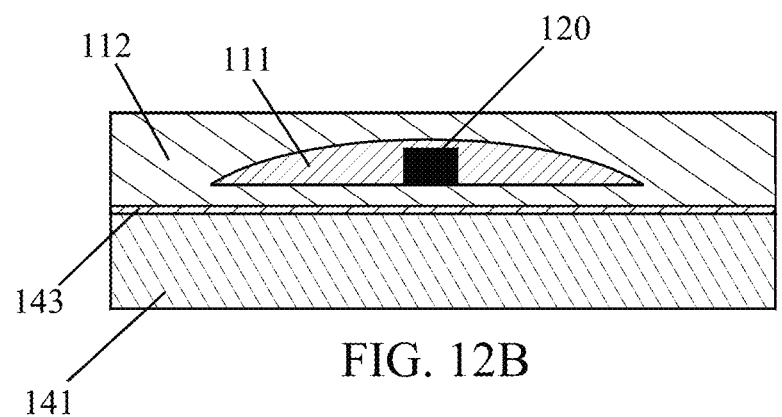
Figure 12C:
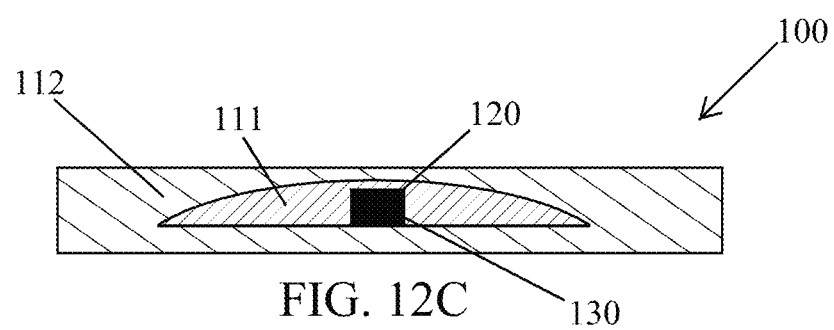

In an alternative fabrication method, as shown in FIGS. 12A-12C, the embedded device 120 is placed on a cured layer of the second portion 112 of the substrate 110. Next, as shown in FIG. 12A, drops of the material for the first portion 111 (PDMS (5:1), for example) are deposited around the device 120. The material can be added manually, or with the aid of equipment such as an inkjet or 3D printer. FIG. 12B shows the material of the second portion 112 of the substrate 110 added. The released integrated device 100 is shown in FIG. 12C.

Figure 13A:
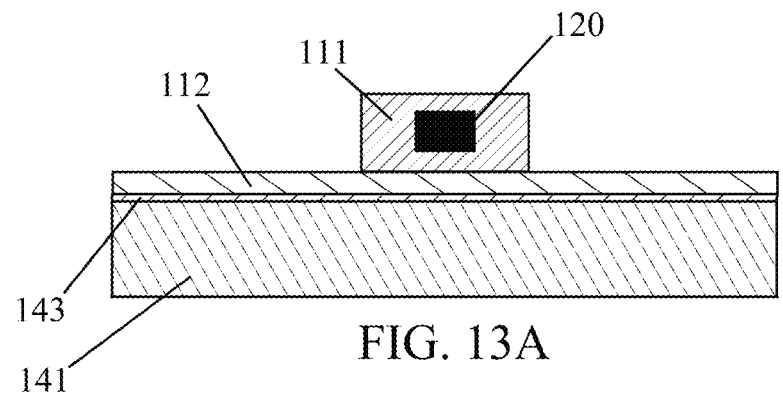
FIGS. 13A-13C depict an alternative fabrication method.
Figure 13B:
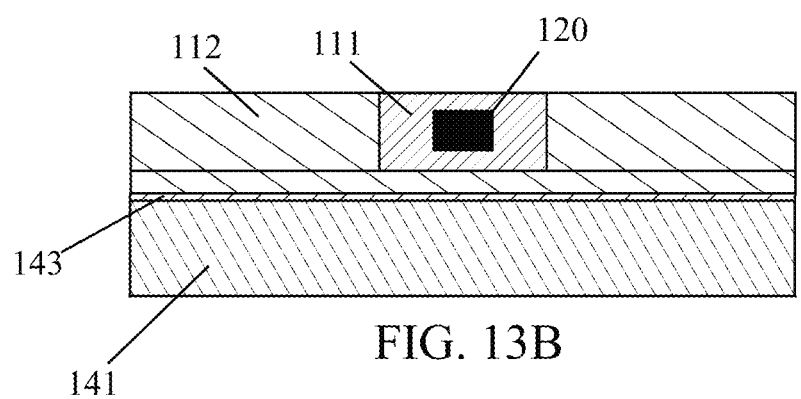
Figure 13C:
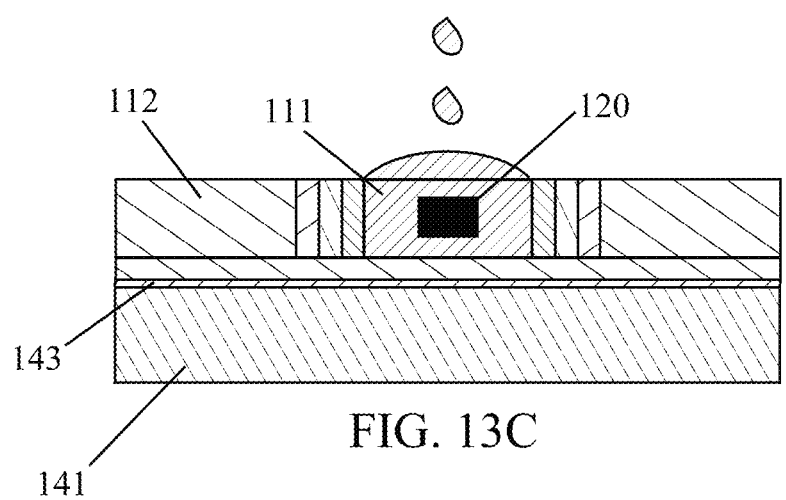

FIGS. 13A-13C depict another alternative embodiment of the fabrication method. First, the rigid electronic device 120 and the first portion 111 of the substrate 110 are fabricated, similar to the method described above, and place on a cured layer of the second portion 112. The composite structure is then surrounded with uncured polymer base, as shown in FIG. 13B. The uncured polymer base may comprise a base material without a curing agent or a base material pre-mixed with a curing agent. As a person having skill in the art will appreciate, the uncured polymer base is generally in a liquid state prior to curing. Drops of curing agent, base material/curing agent mixture, or base material are then deposited at the interface between the first portion 111 and the second portion 112, creating a gradient at the interface of the two portions 111, 112.

In one example of the fabrication process depicted in FIGS. 13A-13C, the rigid device 120 is encapsulated in PDMS (20:1). Next, PDMS (5:1) droplets are deposited manually, such as by a micro-pipette, around the rigid device 120 before curing the PDMS (20:1) substrate 110. The PDMS (5:1) drops diffuse into the surrounding PDMS (20:1). Since the PDMS droplets are located in the center of the structure and PDMS flows from the center to the sides, the concentration of PDMS (5:1) at the center is higher than the edges. In other words, there is a concentration gradient of PDMS (5:1) across the soft substrate 110. Therefore, the mixture of PDMS (20:1) and (5:1) form PDMS (x:1), where x varies between 5 and 20 across the substrate 110.

In yet another alternative, the gradient in stiffness starts at the edge of the first section 111. The fabrication process is similar to the process used to create a two-region substrate, except that for the formation of the gradient in stiffness, where PDMS (5:1) droplets are injected to the center of the structure at the end of the process before curing the second section 112.

Figure 14A:
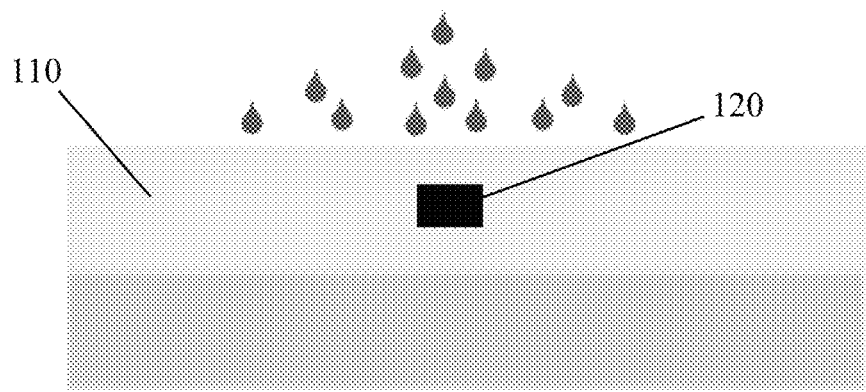
FIGS. 14A-14C show another fabrication method.
Figure 14B:
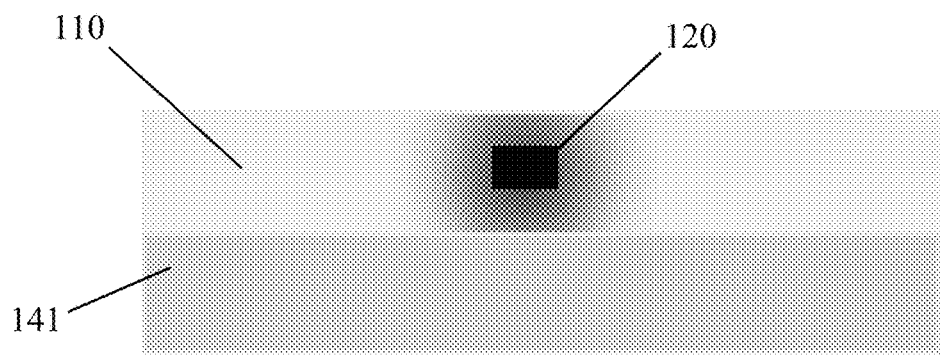
Figure 14C:
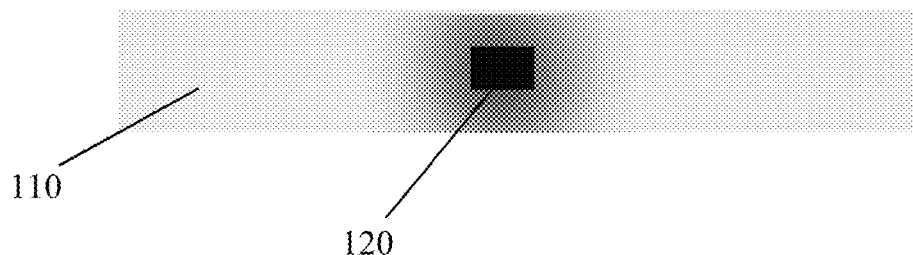
Figure 15A:
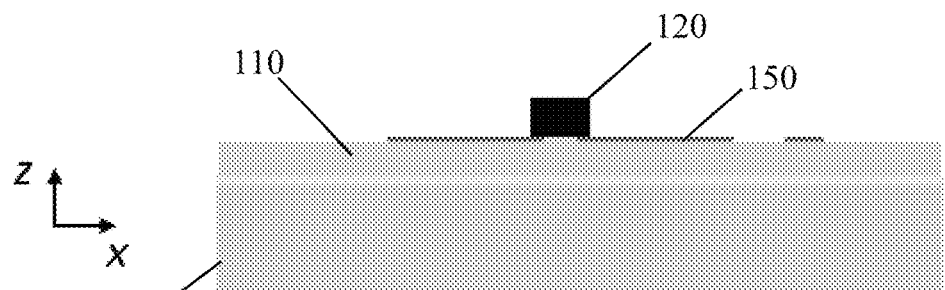
FIGS. 15A-15D depict a fabrication method with the inclusion of passive electronic devices.
Figure 15B:
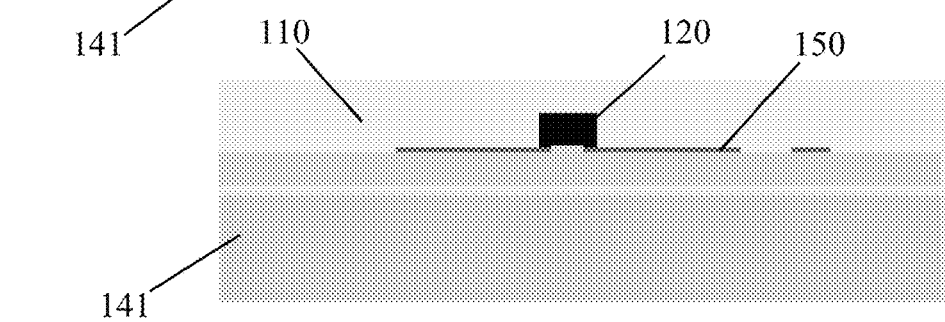
Figure 15C:
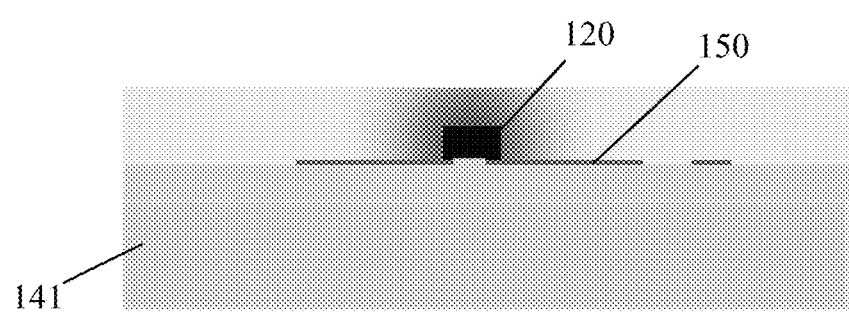
Figure 15D:
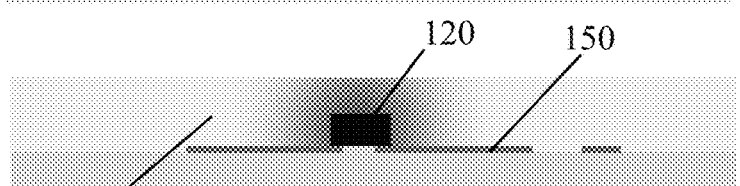

FIGS. 14A-14C show embodiment of the fabrication method with a continuous gradient without a distinct first section 111 and second section 112. In this method, the gradient in stiffness in the substrate 110 is created by diffusing a curing agent into the substrate 110. For example, as shown in FIG. 14A, the device 120 is embedded within the substrate 110, which can be cured or semi-cured. If semi-cured, the substrate 110 may have some portion of the curing agent pre-mixed with the base material. Once the device 120 is embedded in the substrate 110, drops of the curing agent are deposited onto the substrate 110, which will then diffuse into the material comprising the substrate 110. As previously stated, the drops can be added manually or by using an inkjet or 3D printer, where it can diffuse into the substrate 110. The curing agent may be applied by other techniques, such as through the use of an aerosol jet printers or spray jetting systems.

If using a printer or jetting system, the pattern of drops can be programmed digitally to provide any gradient pattern. For example, the printer can make a first pass of depositing a curing agent at the interface 130. A second pass can cover the same area, but also extend beyond the area of the first pass. Subsequent passes can enlarge the area covered by the curing agent in the previous pass. In this manner, the first area will be covered by the most passes and, thus, will have the highest concentration of curing agent, leading to a higher stiffness in the substrate 110.

When using an inkjet printer or aerosol jet printer, additional steps may be performed to aid the process. For example, in one alternative embodiment the curing agent is combined with a solvent, such as xylene, trichlorobenzene, hexane, isopropyl alcohol, or similar solvents to reduce the viscosity of the curing agent. Alternatively, the curing agent could be heated to reduce the viscosity. Other variations of these techniques can be employed to develop an appropriate viscosity and surface tension to allow printing of the curing agent.

Additional steps may also include heating the substrate 110 to control the rate of diffusion of the curing agent into the substrate 110. For example, when the curing agent is printed onto the substrate comprising an uncured base material, the curing agent will diffuse into the base material until cured. The extent of diffusion of the curing agent can be limited by heating the substrate 110, which decreases the curing time. In some embodiments where the substrate 110 is heated sufficiently, the uncured base material will cure upon impact by the curing agent deposited by the printer. Using this technique, the precision of gradients in the stiffness of the substrate 110 can be improved.

Figure 16A:
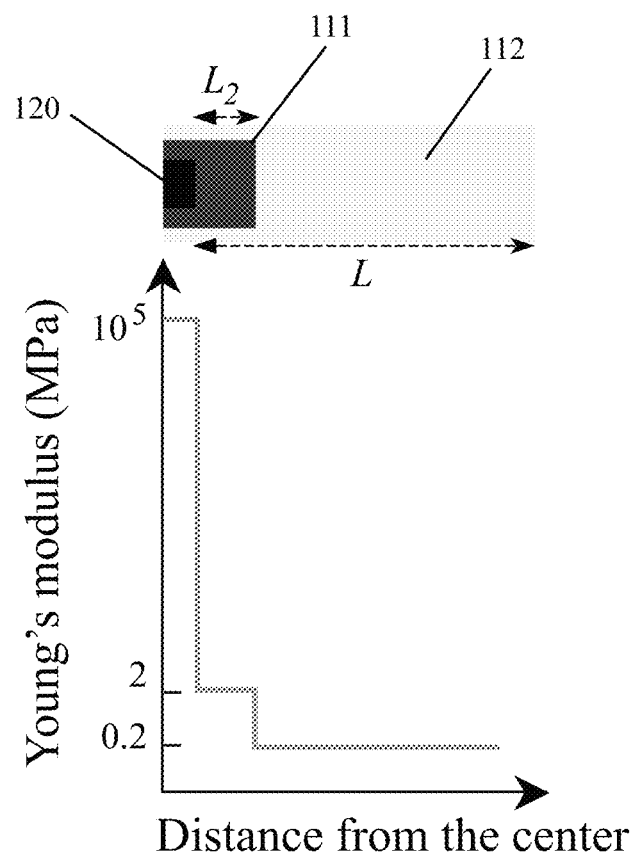
FIGS. 16A-16C are schematics of the Young's modulus of the materials as a function of location along the length of the stretchable substrate, according to different embodiments.
Figure 16B:
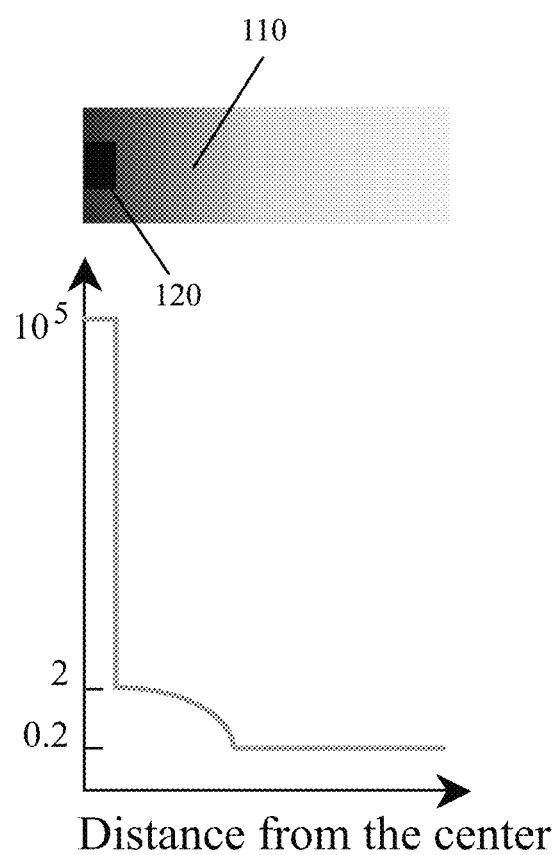
Figure 16C:
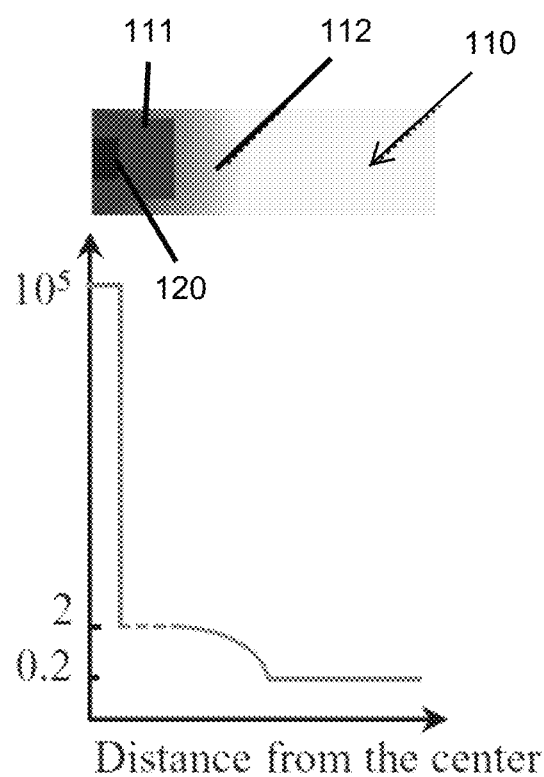

FIGS. 16A-16C show schematics of devices created by several of the processes described above. For example, FIG. 16A shows a device with a substrate 110 comprising a first section 111 and a second section, each having a uniform stiffness. FIG. 16B shows a device with a substrate 110 having a stiffness gradient beginning at the edge of the rigid device 120. FIG. 16C shows a device with a first section 111 having a uniform stiffness and a second section 112 having a stiffness gradient. Further depicted in FIGS. 16A-16C are graphs depicting the Young's modulus of the materials as a function of location along the length of the stretchable substrate 110. The approach depicted in FIG. 16C results in a smoother strain contour with a lower strain around the silicon chip compared to other approaches.

FIGS. 15A-15D show an alternative fabrication embodiment where antennas, coils, and other passive devices 150 are embedded in the substrate 110. As a person having skill in the art will appreciate, several fabrication methods to create a gradient in the substrate 110 can be employed.

In addition to delamination at the interface 130 of the rigid device 120, wiring of the electronic components in an elastic substrate 110 poses an additional challenge. Wires are made of conducting materials having a different Young's modulus from the substrate 110; therefore, these connections experience levels of strain and stress that also require soft substrate engineering. The interfaces between the regions of the substrate 110 are often locations where wires can break. A composite structure of two regions having different values of Young's modulus causes a step in the strain level at the interface. This step in strain induces wire breakage. With gradients in stiffness, the step in the strain level can be reduced, thereby minimizing breakage.

Several of the substrates 110 described herein address the wiring failure that can happen where the wire passes across the substrate regions having different stiffness values. Regions in the substrate 110 experience different levels of expansion and contraction in the direction perpendicular to the applied load. Shear stress at the edges of the interfaces can break the wires. In order to address this issue, the substrate 110 material stiffness can be smoothly transitioned from one region to another. This material gradient reduces the sharp shear stress at the interface between regions. For example, in the embodiment where the first section 111 of the substrate 110 has a uniform stiffness and the second section has a stiffness gradient, there is a smoother strain contour with a lower strain around the rigid electronic device 120. Moreover, a wire embedded in the substrate 110 can remain intact without failure approaching 135% strain. For complicated circuits, curing agent or uncured base material could be applied along wires to create a stiffness gradient around each wire. In one embodiment, the curing agent is printed around the wires prior to curing. In yet another alternative, the curing agent can be printed onto the substrate 110 prior to fabrication of the wires, where the curing agent is deposited in a pattern that replicates the path of the wires. In other words, the curing agent can be applied in a pattern that replicates the wiring pattern in the electronic device 100.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. An integrated electronic device comprising:
a substrate consisting of a polymer base and a curing agent, wherein the substrate has a first section and a second section,
a rigid electronic device is embedded in the substrate,
wherein the first section of the substrate is adjacent to the rigid electronic device and has a uniform stiffness and a higher concentration of curing agent than the second section,
wherein the second section of the substrate is peripheral to the first section and has a stiffness gradient with a maximum stiffness at an interface with the first section,
wherein an average of the Young's modulus of the second section is less than the Young's modulus of the first section, and
wherein the stiffness gradient of the second section is continuous.

2. The integrated electronic device of claim 1, wherein the polymer base comprises an elastic polymer selected from the group consisting of polydimethylsiloxane, two-part silicone elastomer, room-temperature-vulcanizing silicone rubber, tin-catalyzed silicone, and platinum-catalyzed silicone.

3. The integrated electronic device of claim 1, further comprising:
a passive electronic device embedded in the substrate and connected to the rigid electronic device.

4. The integrated electronic device of claim 3, wherein the passive electronic device is at least one selected from the group consisting of an antenna, a coil, a wire, and a sensor.

* * * * *